(12) United States Patent
Hayenga et al.

(10) Patent No.: US 7,867,778 B2
(45) Date of Patent: Jan. 11, 2011

(54) FLUID FOCUSING FOR POSITIONAL CONTROL OF A SPECIMEN FOR 3-D IMAGING

(75) Inventors: Jon W. Hayenga, Kent, WA (US); Paul R. Smargiassi, Woodinville, WA (US)

(73) Assignee: VisionGate, Inc., Gig Harbor, WA (US)

( * ) Notice: Subject to any disclaimer, the term of this patent is extended or adjusted under 35 U.S.C. 154(b) by 288 days.

(21) Appl. No.: 11/678,316

(22) Filed: Feb. 23, 2007

(65) Prior Publication Data
US 2008/0205739 A1 Aug. 28, 2008

(51) Int. Cl.
*G01N 21/00* (2006.01)
*G01N 31/00* (2006.01)
*G01N 1/00* (2006.01)
*G01N 1/10* (2006.01)
*B01L 3/02* (2006.01)
*G06K 9/00* (2006.01)

(52) U.S. Cl. .................... 436/180; 422/81; 422/100; 382/133; 73/864.81

(58) Field of Classification Search ............... 422/73, 422/81, 100, 863.81, 863.71; 436/180
See application file for complete search history.

(56) References Cited

U.S. PATENT DOCUMENTS

| | | | |
|---|---|---|---|
| 3,560,754 A | 2/1971 | Kamentsky |
| 3,705,771 A | 12/1972 | Friedman |
| 3,819,270 A | 6/1974 | Hirschfeld |
| 4,110,043 A | 8/1978 | Eisert |
| 4,293,221 A | 10/1981 | Kay |
| 4,298,836 A | 11/1981 | Groves |
| 4,702,598 A | 10/1987 | Bohmer |
| 4,786,165 A | 11/1988 | Yamamoto |
| 5,034,613 A | 7/1991 | Denk |
| 5,079,959 A | 1/1992 | Miyake |
| 5,117,466 A | 5/1992 | Buican |
| 5,125,737 A | 6/1992 | Rodriguez |
| 5,159,398 A | 10/1992 | Maekawa |
| 5,644,388 A | 7/1997 | Maekawa |
| 5,831,723 A | 11/1998 | Kubota |

(Continued)

OTHER PUBLICATIONS

Zahn, "Microfabricated Microneedles for Minimally Invasive Drug Delivery, Sampling and Analysis," A dissertation submitted in partial satisfaction of the requirement for the degree of Doctor of Philosophy in Engineering-Bioengineering in the Graduate Divisions of the University of California, Berkeley and University of California, San Francisco, Spring 2001.

(Continued)

*Primary Examiner*—Jill Warden
*Assistant Examiner*—Dean Kwak
(74) *Attorney, Agent, or Firm*—Citadel Patent Law; George A. Leone

(57) ABSTRACT

A method for loading a sample for imaging by an optical tomography system. A sample volume including at least one microscopic sample and a viscous fluid is coaxially loaded into a sample delivery tube. The sample volume is impelled through a focus cell into a capillary tube, where the capillary tube has a smaller crossectional area than the sample delivery tube, so that a reduced volume of the at least one microscopic sample and viscous fluid is constrained to a central region within the capillary tube.

3 Claims, 4 Drawing Sheets

U.S. PATENT DOCUMENTS

| | | |
|---|---|---|
| 6,177,277 B1 | 1/2001 | Soini |
| 6,256,096 B1 | 7/2001 | Johnson |
| 6,473,172 B1 | 10/2002 | Pelmulder |
| 6,519,355 B2 | 2/2003 | Nelson |
| 6,522,775 B2 | 2/2003 | Nelson |
| 6,591,003 B2 | 7/2003 | Chu |
| 6,636,623 B2 | 10/2003 | Nelson |
| 6,697,508 B2 | 2/2004 | Nelson |
| 6,741,730 B2 | 5/2004 | Rahn |
| 6,770,893 B2 | 8/2004 | Nelson |
| 6,944,322 B2 | 9/2005 | Johnson |
| 7,075,647 B2 | 7/2006 | Christodoulou |
| 7,197,355 B2 | 3/2007 | Nelson |
| 2004/0022859 A1 | 2/2004 | Chen et al. |
| 2004/0036875 A1 | 2/2004 | Kramer |
| 2004/0076319 A1 | 4/2004 | Fauver |
| 2004/0122371 A1 | 6/2004 | Neer et al. |
| 2004/0220472 A1 | 11/2004 | Harul et al. |
| 2005/0010108 A1 | 1/2005 | Rahn |
| 2005/0085708 A1 | 4/2005 | Fauver |
| 2005/0085721 A1 | 4/2005 | Fauver |
| 2006/0023219 A1 | 2/2006 | Meyer |
| 2006/0096358 A1 | 5/2006 | Fauver et al. |

OTHER PUBLICATIONS

Fauver et al., "Development of Micro-Optical Projection Tomography for 3D Analysis of Single-Cells,"Image Acquisiton and Processing XI. Edited by Conchello, Jose-Angel; Cogswell, Carol. J.; Wilson, Tony. Proceedings of the SPIE, vol. 5324, pp. 171-181 (2001).

Fauver et al., "Three-dimensional imaging of single isolated cell nuclei using optical projection tomography," Optics Express, 4210, vol. 13, No. 11, May 30, 2005.

FLUID FOCUSING FOR POSITIONAL CONTROL OF A SPECIMEN FOR 3-D IMAGING

FIELD OF THE INVENTION

The present invention relates to optical tomographic imaging systems in general, and, more particularly, to optical tomography where a small object, such as a biological cell, for example, is fluidically positioned in a capillary tube for imaging by a microscope.

BACKGROUND OF THE INVENTION

Recent advances in imaging biological cells using optical tomography have been developed by Nelson as disclosed, for example, in U.S. Pat. No. 6,522,775, issued Feb. 18, 2003, and entitled "APPARATUS AND METHOD FOR IMAGING SMALL OBJECTS IN A FLOW STREAM USING OPTICAL TOMOGRAPHY," the full disclosure of which is incorporated by reference. Further development in the field is taught in Fauver et al., U.S. patent application Ser. No. 10/716,744, filed Nov. 18, 2003 and published as US Publication No. US-2004-0076319-A1 on Apr. 22, 2004, entitled "METHOD AND APPARATUS OF SHADOWGRAM FORMATION FOR OPTICAL TOMOGRAPHY," the full disclosure of which is also incorporated by reference.

Processing in such an optical tomography system begins with specimen preparation. Typically, specimens taken from a patient are received from a hospital or clinic and processed to remove non-diagnostic elements, fixed and then stained. Stained specimens are then mixed with an optical gel, inserted into a micro-capillary tube and images of objects, such as cells, in the specimen are produced using an optical tomography system. The resultant images comprise a set of extended depth of field images from differing perspectives called "pseudoprojection images." The set of pseudoprojection images can be reconstructed using backprojection and filtering techniques to yield a 3D tomogram of a cell of interest.

The 3D tomogram then remains available for analysis in order to enable the quantification and the determination of the location of structures, molecules or molecular probes of interest. An object such as a biological cell may be labeled with at least one stain or tagged molecular probe, and the measured amount and location of this probe may yield important information about the disease state of the cell, including, but not limited to, various cancers such as lung, breast, prostate, cervical and ovarian cancers.

In Optical Tomography Microscope (OPTM) systems as described, for example, in Fauver, about 250 sample images taken over a 180 degree rotation are required to adequately sample the volume of a cell nucleus randomly distributed in a flow stream within a 50 micron capillary tube. Due to limitations in the previous cell introduction method, a high number of the cells appear close to the capillary tube walls making the sampling just good enough to render ~0.6 micron resolution at an outer radius.

Because such optical tomography systems use unfocused capillary tube loading techniques, cells and other objects are prone to tracking errors and optical imperfections including geometric distortion and loss of resolution from aberrations induced by tube wall refraction. Such systems are also sensitive to longitudinal movement due to vibration of media, temperature changes, entrapped gas expansion and/or gel instability from chemistry and local rheology changes. Uncentered specimens also tend to stick to walls or move slowly along walls leading to clogging from aggregations of cells attaching to walls. Present systems also suffer from sample carryover problems.

In order to improve throughput, a method for providing higher resolution or improved signal to noise is needed to reduce sampling requirements while maintaining acceptable resolution. The present invention provides new and novel techniques for centering samples and reducing sample volumes to improve image acquisition and throughput in an OPTM system while mitigating sample carryover issues.

SUMMARY OF THE INVENTION

The present invention provides a method for loading a sample for imaging by an optical tomography system. A sample volume including at least one microscopic sample and a viscous fluid is coaxially loaded into a sample delivery tube. The sample volume is impelled through a focus cell into a capillary tube, where the capillary tube has a smaller crosssectional area than the sample delivery tube, so that a reduced volume of the at least one microscopic sample and viscous fluid is constrained to a central region within the capillary tube.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited.

Generally as used herein the following terms have the following meanings when used within the context of optical microscopy processes:

"Capillary tube" has its generally accepted meaning and is intended to include microcapillary tubes and equivalent items with an inside diameter of 100 microns or less. Such microcapillary tubes are manufactured by Polymicro Technologies, LLC., AZ.

"Object" means an individual cell or other entity. One or more objects may comprise a specimen.

"Pseudoprojection" includes a single image representing a sampled volume of extent larger than the native depth-of-field of the optics.

"Specimen" means a complete product obtained from a single test or procedure from an individual patient, (e.g., sputum submitted for analysis, a biopsy, or a nasal swab.) A specimen may be composed of one or more objects. The result of the specimen diagnosis becomes part of the case diagnosis.

"Sample" means a finished cellular preparation that is ready for analysis, including all or part of an aliquot or specimen.

Figure 1A:
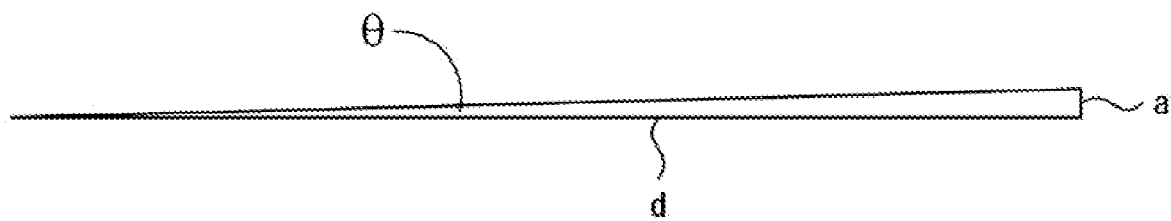
FIG. 1A schematically illustrates a sampling increment for a 50-micron diameter capillary tube using equal sampling increments during acquisition of pseudoprojections by an optical tomography microscope system.
Figure 1B:
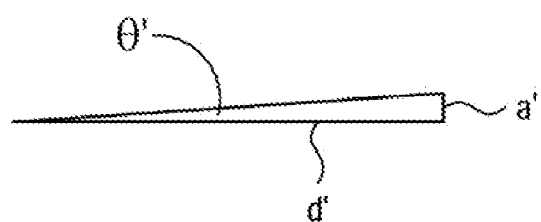
FIG. 1B schematically illustrates a sampling increment for a 15-micron diameter capillary tube using equal sampling increments during acquisition of pseudoprojections by an optical tomography microscope system.

Referring now to FIG. 1A, a sampling increment for a capillary tube with no target centering using equal sampling increments during acquisition of pseudoprojections by an optical tomography microscope system is schematically illustrated. Here the sampling Increment may be described by a first sampling angle, $\theta$, a first sampling distance, d, and a sampling interval, a In one example where the capillary tube diameter is about 50 microns, $\theta$ will be 0.720 degrees, d will be 25 microns, and a will have a value of 0.31 microns. In order to adequately sample an uncentered object under the aforesaid conditions, about 250 samples are required over 180° of rotation of the capillary tube.

Typically, however, a majority of specimen nuclei and cell types to be analyzed in a biological sample such as sputum will be smaller than 25 microns in diameter. In order to constrain the cell's flow stream to within a +/−5 micron radius of the central flow stream, the overall radius to be sampled will be 15 microns or a 30 micron central diameter. Should the sample be constrained to nuclei only, with typical size of 10 microns, the central volume's diameter to be sampled would be 15 microns.

Referring now to FIG. 18, a sampling increment for a 15 micron diameter capillary tube using equal sampling increments during acquisition of pseudoprojections by an optical tomography microscope system is schematically illustrated. Here the sampling increment is constrained by a second, smaller, sampling angle, $\theta'$, a second, smaller, sampling distance, d', and a second sampling interval, a', as allowed by centering the sample using the systems and methods of the present invention. For example, maintaining a consistent 0.6 micron sampling interval a', the number of samples for a 30 micron core can be reduced from 250 to 150. Using a 15 micron central diameter target the sampling can be further reduced to 75 samples. The improvement in system throughput will scale directly to the percent reduction in image sampling required. Thus, there is a significant performance advantage to centering target objects, such as cells, within a capillary tube for optical tomography analysis, because higher resolution with improved signal-to-noise ratios can be achieved with the same or smaller rotational sample increment. Alternatively, the rotational sample increment can be reduced to yield fewer samples for the same volume while maintaining sufficient image quality.

Figure 2:
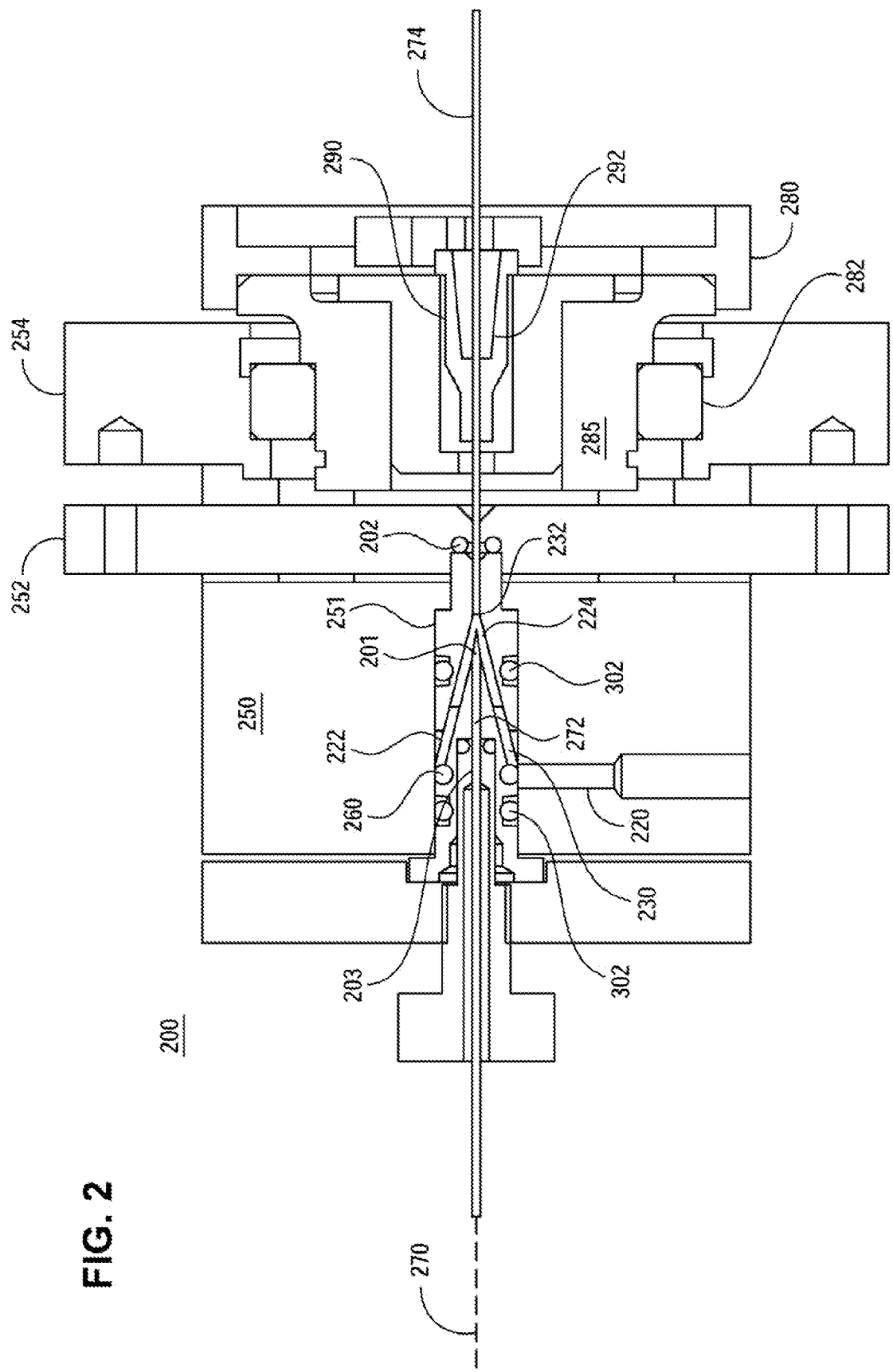
FIG. 2 schematically shows a crossectional view of a rotating high-pressure hydrodynamic focus flow cell as used in one example embodiment of the invention.

Referring now to FIG. 2, there shown schematically is a crossectional view of a rotating high pressure hydrodynamic focus flow cell as used in one example embodiment of the invention. The rotating high-pressure hydrodynamic focus flow cell 200 includes a case 250, a seal housing 252, and a bearing race 254. The case 250 includes a tube 251, where the tube 251, in turn, houses components including a focus cell 222, a syringe needle nozzle injector 201, and a needle seal 203. The focus cell 222 further includes a ribbed conical section 230, first and second o-rings 302 and tapered flow cell 224.

A sheath fluid injection port 220 is bored or otherwise made in the case 250 to be in fluid communication with the ribbed conical section 230 at a sheath fluid input channel 260. The seal housing 252 centrally holds a rotating seal 202 that is axially aligned to accept a sample delivered by a syringe needle 272 inserted through the tapered flow cell 224. The tapered flow cell 224 terminates at a capillary tube outlet 232. In a preferred embodiment, the syringe needle 272 comprises a replaceable injector needle. The replaceable injector needle advantageously reduces carryover issues and also reduces the overall cleaning volume that must be flushed through a system to assure the specimen minimal carry over.

The bearing race 254 holds a rotation bearing 282 in a pressure fit against a shaft housing 285. A shaft 290 is centrally mounted in the shaft housing 285. The shaft 290 has a bore for accepting a replaceable capillary tube 274 that is also axially aligned. A drive gear 280 is adapted to engage the shaft housing 285. The drive gear 280 includes an elongated annular tapered element 292 constructed to accept and centrally hold the replaceable capillary tube 274 in line with the central axis 270. The case 250, seal housing 252, tube 251 and shaft 290 are linearly aligned along a central axis 270.

Figure 3:
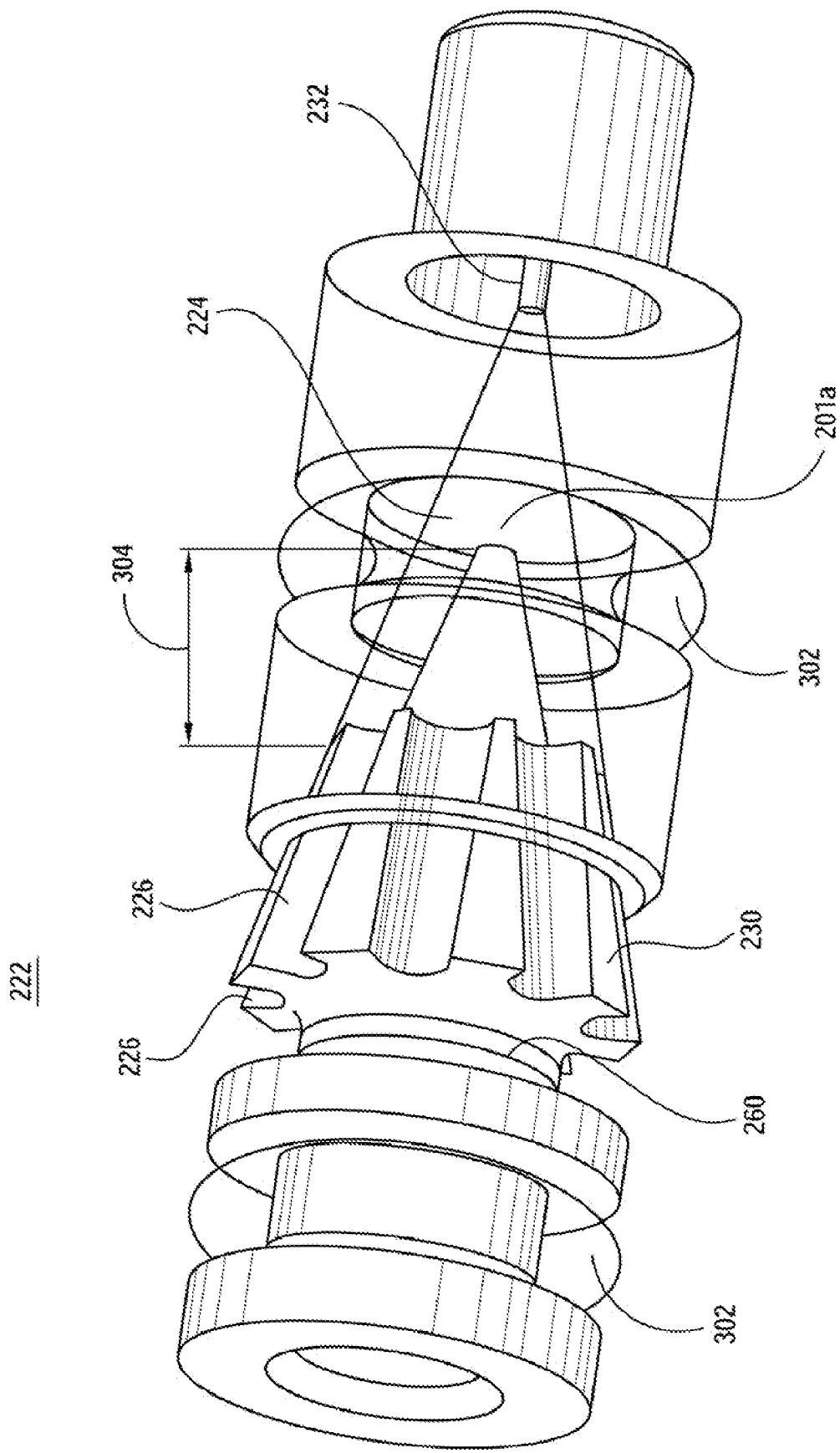
FIG. 3 schematically shows a detailed perspective view of a focus cell as used in a rotating high pressure hydrodynamic focus flow cell in one example embodiment of the invention.

Referring now to FIG. 3, there shown schematically is a more detailed transparent perspective view of a focus cell as used in a rotating high pressure hydrodynamic focus flow cell as used in one example embodiment of the invention. When inserted into focus cell 222, the syringe needle nozzle injector 201 (shown in FIG. 2) fits within the ribbed conical section 230 at needle location 201a with o-ring seals 302 on both ends and positioned at the center of the tapered flow cell 224. The ribbed conical section 230 tapers down along the flow direction and is uniformly ribbed with a plurality of sheath injection ports 226. The plurality of sheath injection ports 226 are positioned to allow sheath gel to be delivered from fluid input channel 260, through the plurality of sheath injection ports 226 to the tapered flow cell 224.

Using the rotating high pressure hydrodynamic focus flow cell of the present invention, specimen centering results from a centered flow produced by coaxially joining two streams under laminar flow conditions. Laminar flow may be described by the relationships:

R=Reynolds number<<2000, where R=(density)(Velocity)(Diameter)/viscosity.

Ideally the flow velocities are matched or nearly matched at the injection location. When flow velocities are equal the initial core diameter to sheath diameter ratio will be preserved. At the point where the central flow and outer, "sheath," flow streams are joined, the flow streams assume the same flow profile. As flow transitions down the conical flow profile of the hydrodynamic focusing cell, the velocity of the fluid increases to support the constant mass flow through the taper. As the velocity increases the fluid is extruded into a much smaller diameter, but the flow streams retain the same relative position across the flow profile. Particulate in the central flow streams will remain in the central flow streams.

Referring now jointly to FIG. 2 and FIG. 3, in operation, the high pressure hydrodynamic focus cell 200 creates a rotating seal 202 at the capillary tube outlet 232 of the tapered flow cell 224. The rotating seal 202 is constructed using known engineering design techniques to withstand the pressures required to push a highly viscous gel through the close fit replaceable capillary tube 274. Typical pressures can exceed 1000 PSI. The rotation bearing 282 allows the close fit replaceable capillary tube 274 to be rotated via a belt and motor (not shown) while still sealed by the o-ring 202 around a needle 272.

A sheath fluid (not shown) is injected into the sheath fluid injection port 220 through the fluid input channel 260 and into the plurality of sheath injection ports 226 to form separate sheath flow streams. At substantially the same time, the syringe needle 272 delivers a sample through the syringe needle nozzle injector 201 at needle location 201a. A distance 304 between an output end 305 of conical section 230 and the output of syringe needle nozzle injector 201 is enough to allow the separate sheath flow streams to create a fully formed joined flow profile. The sheath fluid and sample flow streams join coaxially at an output end of syringe needle nozzle injector 201. When the drive gear 280 rotationally engages the shaft housing, the syringe needle 272 in cooperation with the sheath fluid ports can deliver a coaxially joined sheathed sample volume through the syringe needle nozzle injector 201 to the replaceable capillary tube 274 inserted at the capillary tube outlet 232.

In a preferred embodiment, the gel media for carrying the sample should exhibit high viscosity and thixotropic properties suitable for retaining the central core of sample once it is injected into the central region of the gel media in the syringe. Particles once loaded into a syringe core will extrude down a capillary tube with the particles remaining in the central flow stream via laminar flow down the capillary tube, Additionally, the tapered delivery transition piece, tapered flow cell 224, creates a smooth transition from the syringe flow to the capillary tube inside diameter.

The gel media may also advantageously be an optical gel selected to match the refractive index of the capillary tube. Index matching materials are commercially available (e.g. commercial sources include Nye Optical Gels, Dymax Corp, and Cargille Labs) and include, for example optical gels, oils and fluids of varying indices of refraction for reducing light reflection at optical interfaces, Optical gels are particularly useful where higher viscosity is desired and may comprise a medium of oil, gel, polymer epoxy, or other optically transparent materials that matches refractive indices of the surroundings. Specimens can be held in index-matching epoxy, embedding media, or plastic polymer as well as index-matching gels and viscous fluids.

Use of the hydrodynamic focus cell of the present invention also allows reducing the number of samples required for reconstruction, thereby improving data collection speed from 1.6 to as much as 3.3 times faster than without hydrodynamic focusing. The hydrodynamic focus cell of the invention facilitates centering of a specimen which reduces tracking errors and dynamic range of focus tracking required, and substantially reduces tube wall optical effects including geometric distortion and loss of resolution from aberrations induced by wall refraction. At the same time, the system of the invention allows increasing the overall diameter of capillary tubes for holding specimens making the overall OPTM system less sensitive to longitudinal movement due to factors like vibration of the gel, temperature changes, entrapped gas expansion or gel instability from chemistry or local rheology changes.

The system of the present invention improves reliability by the reducing the tendency of specimen to stick to walls or move slowly along walls, thereby reducing clogging from aggregations of cells attaching to walls. Hydrodynamic focus inherently causes cells to pull apart longitudinally, thereby reducing clogging and improving presentation to a microscope by reducing the probability that cells will be close together. The Reynolds number in a small diameter capillary tube remains below 20 even at higher velocities making high throughput possible without turbulence upsetting the centering of the specimen.

Figure 4:
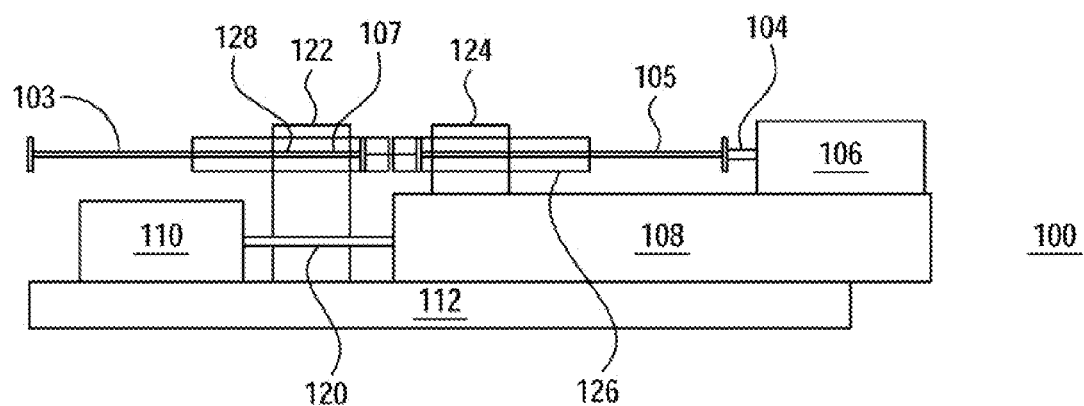
FIG. 4 schematically shows an example illustration of an alternate mechanism of the invention for central core loading a syringe at the start of a loading sequence.

Referring now to FIG. 4 an example illustration of an alternate mechanism of the invention for central core loading a syringe at the start of a loading sequence is schematically shown. A central core loading mechanism 100 includes a first syringe A having a plunger 103 mounted by a first syringe barrel grip 122 to a base 112. A second syringe B having a plunger 105 is mounted by a second syringe barrel grip 124 to a linear slide 108. The syringe B plunger 105 is coupled to a first linear actuator shaft 104 in a first linear actuator 106, where the first linear actuator 106 is mounted on linear slide 108. Linear slide 108 is, in turn, slideably mounted to the base 112. A second linear actuator 110 is coupled to transversely move a shaft 120, where the shaft 120 is attached to transversely move linear slide 108. Syringe B has a small outer diameter needle 107 suitably sized to insert into the center of syringe A and a syringe barrel 126.

The first syringe barrel grip 122 may advantageously be fixed to the base plate 112 to provide accuracy in the stroke of the plunger 105 relative to the syringe barrel 126. In one example, the syringe barrel grip 122 is constructed of a rigid material such as aluminum or the like, or other known materials, and shaped to fit a standard U-100 syringe barrel. An adapter or fitting may be used to adjustably connect the linear actuator shaft 104 to the syringe plunger 105. The first and second linear actuators 106, 110 may comprise, for example, unipolar stepper motor encasements that convert electrical pulses to linear, mechanical strokes of the linear actuator shafts 104, 120.

In typical use, syringe A contains a media gel and syringe B contains a sample, where the sample typically comprises biological cells held in an optical gel. Prior to loading the sample into syringe A, the small outer diameter needle 107 of syringe B is inserted into the center of syringe A.

Figure 5:
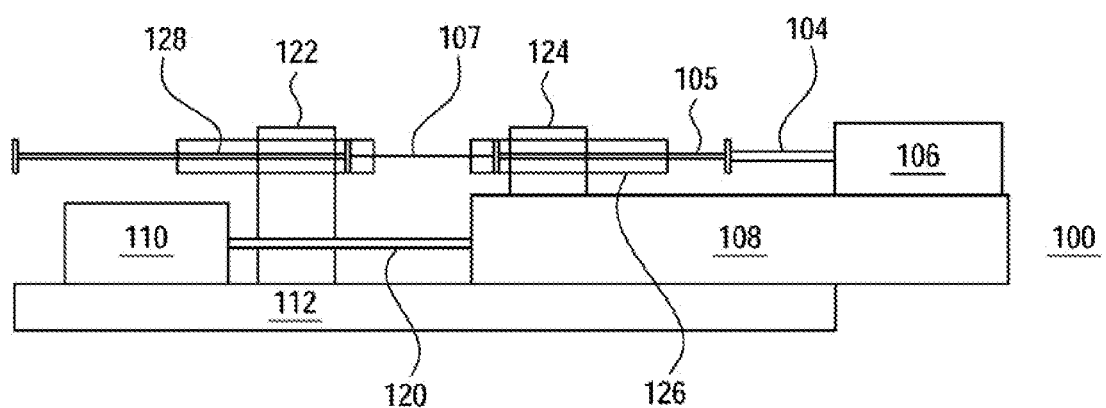
FIG. 5 schematically shows an example illustration of an alternate mechanism of the invention for central core loading a syringe at the end of a loading sequence.

Referring now to FIG. 5, an example illustration of an alternate mechanism of the invention for central core loading a syringe at the end of a loading sequence is schematically shown. In operation, syringe B is retracted from syringe A using the controlled first actuator 110 to push out linear slide 108, while the controlled second linear actuator 106 pushes syringe B to dispense an equal volume of sample as the volume of the needle 107 that is being retracted from syringe A. In this way, a sample is loaded into a central core 128 of syringe A for later dispensing into an optical tomography capillary tube (not shown) for observation.

The high viscosity of the fluids used in syringes A and B, and relatively small dimensions of both the syringes and capillaries used in the optical tomography sample delivery assure low Reynolds numbers for the flows within the sample delivery system. The rheological properties of high viscosity and thixotropic sample media allow the suspension of cells without settling and the stopping of flow to allow rotation of the sample capillary tube without disturbing the angular or longitudinal (i.e. flow axis dimension) of the sample. A sample loaded into the syringe pump in a coaxial manner so that it is constrained to a central core of the sample delivery tube will not experience turbulence, especially in a delivery system where the transition to capillary tube is tapered and smooth. A syringe central core load of this type can be pumped through a capillary tube retaining the relative radial position of the cells. Cells that start in the center of a laminar flow system will maintain that central flow stream. As the flow stream constricts from a few millimeters in diameter down to less than 100 microns, the central particles will remain in the center. The rheological response of a thixotropic non-newtonian fluid like the gel media in which the cells are embedded creates a thinning of the fluid along the walls where shear is greatest as gel begins to flow. The result of this shear thinning nearest the wall has the effect of creating a flatter velocity flow profile that leaves central particles undisturbed by differential flow velocities across their diameter.

Having described the fluid focusing systems contemplated by the invention, an example of a method of the present invention for loading a reduced sample volume for imaging by an optical tomography system will now be described. A sample volume, including at least one microscopic sample and a viscous fluid, may be coaxially loaded into a sample delivery tube, such as tube 251. The sample volume may then be impelled through a tapered delivery transition piece, such as tapered flow cell 224 into a capillary tube 274. The capillary tube has a smaller crossectional area than the sample delivery tube, so that a reduced volume of the at least one microscopic sample and viscous fluid is constrained to a central region within the capillary tube. Preferably, the sample volume is formed by coaxially joining two streams under laminar flow conditions wherein one of the two streams contains the at least one microscopic sample. According to one aspect of the method of the invention, the two streams are joined under laminar flow conditions by separately injecting the two streams into either a tapered flow tube or a hydrodynamic focus cell.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A method for loading a sample for imaging by an optical tomography system comprising the steps of:

loading a sample volume including at least one microscopic sample into a sample delivery tube;

coupling the sample delivery tube to a hydrodynamic focus cell with a nozzle injector, where the hydrodynamic focus cell includes a plurality of sheath injection ports and a capillary tube outlet;

injecting a sheath fluid into the plurality of sheath injection ports to form separate sheath flow streams and delivering the sample volume through the nozzle injector while maintaining a distance between an output end of the plurality of sheath injection ports and an output of the nozzle injector so that the sheath fluid and sample flow streams join coaxially at the output end of the nozzle injector to create a coaxially joined sheathed sample volume;

while injecting, simultaneously and continuously axially rotating a capillary tube inserted into a rotating seal coupled to receive the coaxially joined sheathed sample volume; and impelling the coaxially joined sheathed sample volume through the rotating seal into the continuously axially rotating capillary tube, where the continuously axially rotating capillary tube has a smaller cross-sectional area than tapered flow cell at the position of the sample injector, and where the hydrodynamic focus cell includes a tapered flow cell so that a reduced volume of the at least one microscopic sample and sheath fluid is constrained to a central region within the rotating capillary tube, and where the plurality of sheath injection ports, the sample delivery tube, the rotating capillary tube and the continuously axially rotating seal are axially aligned along a central axis and the continuously axially rotating capillary tube is rotated with the rotating seal around the central axis;

wherein a rotation bearing allows the capillary tube to be rotated via a belt and motor.

2. The method of claim 1 wherein the sheath fluid comprises a non-newtonian shear thinning gel.

3. The method of claim 1 wherein the tapered flow cell terminates at a capillary tube inlet, and the plurality of sheath injection ports and the tapered flow cell are axially aligned along a central axis; and the sample delivery tube comprises a nozzle injector having an output end, the nozzle injector being axially centered with respect to the tapered flow cell.

* * * * *